United States Patent
Sati (10) Patent No.: US 10,580,533 B2
(45) Date of Patent: Mar. 3, 2020

(54) IMAGE-BASED FOOD ANALYSIS FOR MEDICAL CONDITION WARNINGS

(71) Applicant: INTERNATIONAL BUSINESS MACHINES CORPORATION, Armonk, NY (US)

(72) Inventor: Marwan Sati, Mississauga (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 62 days.

(21) Appl. No.: 15/852,156

(22) Filed: Dec. 22, 2017

(65) Prior Publication Data

US 2019/0198173 A1   Jun. 27, 2019

(51) Int. Cl.
| | |
|---|---|
| *G16H 50/30* | (2018.01) |
| *G06T 7/00* | (2017.01) |
| *G16H 20/60* | (2018.01) |
| *G06K 9/62* | (2006.01) |
| *G06K 9/78* | (2006.01) |
| *A61M 5/172* | (2006.01) |
| *G16H 40/60* | (2018.01) |
| *G06F 16/583* | (2019.01) |

(52) U.S. Cl.
CPC .......... *G16H 50/30* (2018.01); *A61M 5/1723* (2013.01); *G06K 9/6256* (2013.01); *G06K 9/78* (2013.01); *G06T 7/0004* (2013.01); *G16H 20/60* (2018.01); *A61M 2205/3306* (2013.01); *A61M 2205/3569* (2013.01); *A61M 2205/50* (2013.01); *A61M 2230/201* (2013.01); *A61M 2230/63* (2013.01); *G06F 16/5854* (2019.01); *G06T 2207/30128* (2013.01); *G16H 40/60* (2018.01)

(58) Field of Classification Search
CPC ... G06T 7/0002; G06T 7/0004; G06T 7/0012; G06T 2207/30128; G06K 2209/17; G16H 20/60; G16H 50/30
See application file for complete search history.

(56) References Cited

U.S. PATENT DOCUMENTS

| | | | |
|---|---|---|---|
| 8,690,578 B1* | 4/2014 | Nusbaum et al. | G09B 19/00 434/127 |
| 2011/0130746 A1* | 6/2011 | Budiman | A61B 5/14532 604/890.1 |
| 2011/0318717 A1* | 12/2011 | Adamowicz | G16H 20/60 434/127 |

(Continued)

FOREIGN PATENT DOCUMENTS

WO   WO-2017/015612 A1 *   1/2017   ............. G06Q 50/12

*Primary Examiner* — Andrew W Johns
(74) *Attorney, Agent, or Firm* — Michael Best & Friedrich LLP (57) ABSTRACT

A method of performing image based analysis of food. The method includes receiving, with an electronic processor, image data captured by an image capture device, analyzing the image data to identify a food represented in the image data, and determining a characteristic of the food identified in the image data. The method further includes accessing medical information of a user, determining a level of risk associated with the user ingesting the food identified in the image data based on the medical information of the user, and outputting a notification, where the notification providing information related to the level of risk associated with the user ingesting the food identified in the image data.

11 Claims, 3 Drawing Sheets

(56) References Cited

U.S. PATENT DOCUMENTS

2016/0350514 A1* 12/2016 Rajendran et al. .... G06Q 10/10
2019/0073448 A1*  3/2019 Kochura et al. ....... G16H 50/30
2019/0139440 A1*  5/2019 Saito ..................... G06Q 50/22

* cited by examiner

IMAGE-BASED FOOD ANALYSIS FOR MEDICAL CONDITION WARNINGS

FIELD

Embodiments described herein relate to systems and methods for automatically processing images of food to determine ingredients in the food and automatically warning a user when at least one of the ingredients conflicts with a medical condition of the user. Embodiments described herein also relate to automated food detection, automated reading and analyzing of food labels, and automated reading and analyzing of recipes.

SUMMARY

Patients often have medical conditions for which diet is an issue. What foods (including beverages and other liquids) a patient may ingest could exacerbate a medical condition. However, patients may not always be aware of all the potential problems presented by different foods, especially with regard to their own already-identified medical conditions. As a result, patients may ingest foods that end up exacerbating a medical condition or causing side effects or symptoms to manifest.

Accordingly, embodiments described herein provide methods and systems for performing image-based identification of food that is correlated with patient medical information, such as electronic medical record information, to determine a level of risk of the ingestion of the food by the patient with regard to the patient's personal medical conditions.

For example, one embodiment provides a method of performing image based analysis of food. The method includes receiving, with an electronic processor, image data captured by an image capture device, analyzing the image data to identify a food represented in the image data, and determining a characteristic of the food identified in the image data. The method further includes accessing medical information of a user, determining a level of risk associated with the user ingesting the food identified in the image data based on the medical information of the user, and outputting a notification, where the notification providing information related to the level of risk associated with the user ingesting the food identified in the image data.

Another embodiment provides a system for performing image based analysis of food. The system includes an electronic processor configured to receive image data capture by an image capture device, analyze the image data and identify a food represented in the image data, and determine a characteristic of the food identified in the image data. The processor is further configured to determine a level of risk associated with the user ingesting the food identified in the image data based on the medical information of the user, and output a notification providing information related to the level of risk associated with the user ingesting the food identified in the image data.

Yet a further embodiment provides non-transitory computer readable medium storing instructions that, when executed by an electronic processor, perform a set of functions. The set of functions includes receiving image data captured by an image capture device, analyzing the image data to identify a food represented in the image data, and determining a characteristic of the food identified in the image data by accessing a food database containing a library of foods and associated characteristics of the foods. The set of functions further includes accessing medical information of a user, determining a level of risk associated with the user ingesting the food identified in the image data based on the medical information of the user, and communicating with a medical device to prepare a dosage of medicine based on the level of risk.

Other aspects of the invention will become apparent by consideration of the detailed description and accompanying drawings.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, a user may have a medical condition that limits what food the user can consume. As used in the present application, the term "food" includes both solid foods and beverages in liquid form. It may sometimes be difficult for a user to identify whether particular food is restricted and, in some embodiments, it may be difficult for a user to remember or understand what foods are restricted for the user's medical condition. As used herein, a medical condition may include but is not limited to food allergies or intolerances, diseases (such as diabetes), diet restrictions (such as a low-sodium diet, a gluten-free diet, a low-carb diet, or the like), or a combination thereof. Accordingly, embodiments described herein automatically correlate food information from image identification of food with a user's personal medical condition to generate notifications (warnings) specific to a user.

Figure 1:
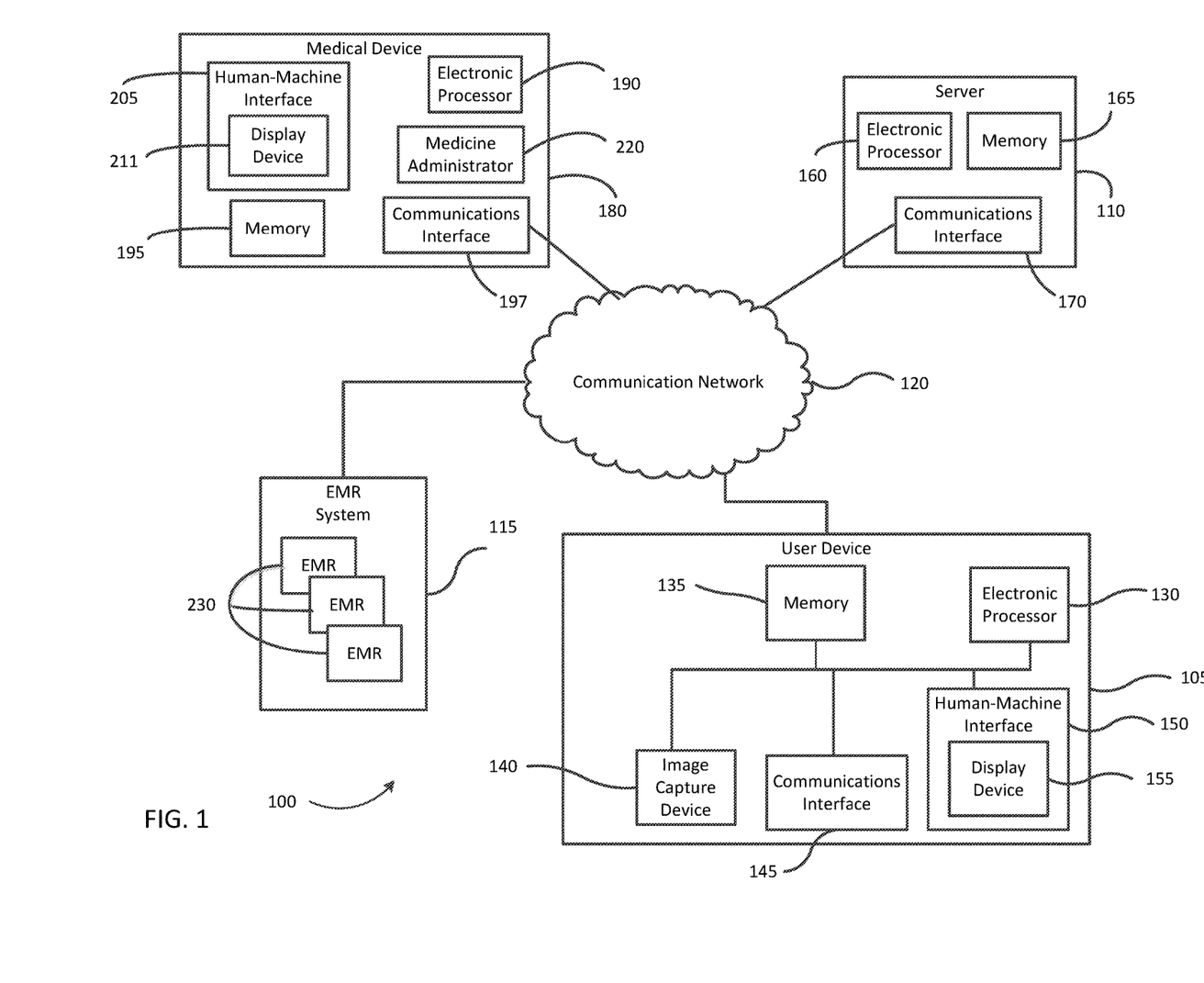
FIG. 1 schematically illustrates a system for performing image-based analysis of food according to one embodiment.

For example, FIG. 1 illustrates a system 100 for performing image-based analysis of food according to one embodiment. The system 100 includes a user device 105, a server 110, and an electronic medical record (EMR) system 115. As will be described in greater detail below, in some embodiments, the system 100 further includes a medical device 180, such as an insulin pump, that administers medication to a user. As illustrated in FIG. 1, in some embodiments, the user device 105, the server 110, the EMR system 115, and the medical device 180 are communicatively coupled via a communication network 120. However, in other embodiments, the user device 105, the server 110, the EMR system 115, the medical device 180, or a combination thereof communicate via one or more dedicated wire connection or other forms of wired and wireless electronic communication. Also, in some embodiments, these components (or a subset thereof) may communicate over multiple types of communication networks. For example, in some embodiments, the user device 105 communicates with the server 110 over the Internet and communicates with the medical device 180 over short-range wireless connection, such as a Bluetooth connection. Also, in some embodiments, the user device 105, the server 110, the EMR system 115, and the medical device 180 may communicate through one or more intermediary devices. For example, as described in more detail below, in some embodiments, the user device 105 may communicate with an intermediary device (such as a smart phone) to communicate with the server 110, the EMR system 115, or both. Also, in some embodiments, the functionality described herein as being provided by the server 110 may be distributed among multiple devices, such as multiple servers included in a cloud service or computing environment.

It should be understood that the system 100 illustrated in FIG. 1 is one example, and the system 100 may include additional or fewer components in various configurations in some embodiments. For example, in some embodiments, the functionality described herein as being performed by the server 110 may be performed by the EMR system 115, the user device 105, or both, which may eliminate the need for the separate server 110. For example, in some embodiments, system 100 may not include the server 110, the EMR system 115, or both. Rather, the functionality as described herein may be provided by a dedicated software application executed by the user device 105. Also, in some embodiments, the EMR system 115 may be included in another system, such as a hospital information system (HIS). Furthermore, the system 100 illustrated in FIG. 1 includes a single user device 105. However, in other embodiments, multiple user devices 105 may be included in the system 100 and may each submit a request for image-based food analysis as described herein.

The user device 105 is an electronic device, such as, for example, a desktop computer, a smartphone, a tablet computer, a smart wearable, a smart television, a smart scale, or the like. In some embodiments, the user device 105 is portable or handheld, which allows a user to carry the user device 105 to different locations where the user may consume food. For example, in some embodiments, the user device 105 is a fitness tracking wearable that tracks physical activity of a user.

As illustrated in FIG. 1, the user device 105 includes an electronic processor 130, a memory 135, an image capture device 140, a communications interface 145, and a human-machine interface 150. The electronic processor 130, the memory 135, the image capture device 140, the communications interface 145, and the human-machine interface 150 are communicatively coupled via a wireless connection, a dedicated wired connection, a communication bus, or the like.

The electronic processor 130 may be a microprocessor, an application-specific integrated circuit (ASIC), or other suitable electronic device. The memory 135 includes non-transitory computer-readable medium, including, for example, read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, other suitable memory devices, or a combination thereof. The electronic processor 130 executes computer-readable instructions ("software") stored in the memory 135. The software may include firmware, one or more applications, program data, filters, rules, one or more program modules, and other executable instructions. For example, the software may include instructions and associated data for performing a set of functions including the methods described herein.

The image capture device 140 includes one or more still or video cameras (visual-light cameras, infrared cameras, or the like) configured to capture image data. Image data can include an image of the food, food label, or a recipe. In some embodiments, the image capture device 140 is embedded in a housing of the user device 105. However, in other embodiments, the image capture device 140 is external to a housing of the user device 105 and communicates with the user device 105 over a dedicated wired or wireless connection or over a communications network, such as via Bluetooth.

The communications interface 145 allows the user device 105 to communicate with devices external to the user device 105. For example, as illustrated in FIG. 1, the user device 105 may communicate with the server 110, the EMR system 115, or both through the communications interface 145. The communications interface 145 may include a port for receiving a wired connection to an external device (for example, a universal serial bus (USB) cable and the like), a transceiver for establishing a wireless connection to an external device (for example, over one or more communication networks 120, such as the Internet, a local area network (LAN), a wide area network ("WAN), and the like), or a combination thereof. As noted above, in some embodiments, the communications interface 145 included in the user device 105 may be configured to communicate with the server 110, the EMR system 115, or both through one or more intermediary devices. For example, in some embodiments, the communications interface 145 included in the user device 105 is a short-range wireless transceiver, such as a Bluetooth transceiver, that communicates with another user device, such as a smartphone, which includes a communications interface for communicating with the server 110, the EMR system 115, or both.

The human-machine interface 150 includes one or more input devices, output devices, or a combination thereof. For example, the human-machine interface 150 may include a keyboard, a cursor-control device (a mouse), a touch screen, a scroll ball, a mechanical button, a display device (a liquid crystal display (LCD)), a printer, a speaker, a microphone, a vibration engine, or a combination thereof. As illustrated in FIG. 1, in some embodiments, the human-machine interface 150 includes at least one display device 155, which may be used to display a notification as described herein.

The server 110 is also an electronic device that includes an electronic processor 160, a memory 165, and a communications interface 170 similar to the electronic processor 130, the memory 135, and the communications interface 145 described above with respect to the user device 105. These components allow the server 110 to communicate with external devices (including the user device 105 and the EMR system 115) and, as described below in more detail, process image data and determine whether one or more notifications should be output on the user device 105 regarding whether the user should or should not consume food identified in the image data.

The medical device 180 is also an electronic device that includes an electronic processor 190, a memory 195, and a communications interface 197 similar to the electronic processor 130, the memory 135, and the communications interface 145 described above with respect to the user device 105. These components allow the medical device to communicate with external devices (including the user device 105, the server 110, or both). In some embodiments, the medical device 180 also includes a human-machine interface 205 with a display device 211 similar to the human-machine interface 150 and display device 155 described above with respect to the user device 105. In addition, the medical device 180 includes a medicine administrator 220, which administers a medicine to a user. Administering the medicine may include preparing (measuring) a dosage of the medicine, automatically administering the dosage of the medicine to the user (through injection or the like), or both. In some embodiments, some of all of the components of the medical device 180 may be included in the user device 105. For example, in some embodiments, the electronic processor 190, the memory 195, and the human-machine interface 205 are integral with the user device 105, while the medicine administrator 220 is a separate unit from the user device 105.

The medicine administrator 220 may include a reservoir housing a supply of the medicine, a measuring unit for measuring the amount of medicine to be administered, an injection unit (including a pump, a needle, or the like) for delivering or injecting the medicine to the user, an actuator for initiating the administration of the medicine, or a combination of these components. The actuator may be actuated manually or automatically. Furthermore, in some embodiments, the medicine administrator 220 includes a pump for injecting medicine into the user, an electric pulse system, or other medical equipment configured to medicate a user. In some embodiments, the medicine administrator 220 can include sensors or other devices intended to detect a biological parameter of a user. For example, the medicine administrator 220 can include a glucose sensor for determining the glucose level of a user's blood. The medicine administrator 220 may be a separate unit from the other components of the medical device 180, or may be integral with the other components of the medical device 180. For example, in some embodiments, the medicine administrator 220, is implanted within the user and wirelessly communicates with the other components. The medicine administrator 220 can administer one or more type of medicine, including but not limited to, insulin, anti-inflammatories, pain medication, allergy medications (for example, for lactose, gluten, or other allergic intolerances), electric pulses, or the like.

To determine whether food identified in received image data conflicts with a medical condition of the user, the server 110 may be configured to access medical data regarding the user, such as an electronic medical record (EMR) associated with the user. In particular, as illustrated in FIG. 1, the EMR system 115 stores one or more EMRs 230. The EMR system 115 may also include similar components as the user device 105 and the server 110. In particular, the EMR system 115 may include an electronic processor, a memory (for storing the EMRs 230), and a communications interface for communicating with the server 110, the user device 105, or both.

As described in more detail below, the user device 105 (via the image capture device 140) captures image data of food and transmits the image data to the server 110, which analyzes the image data using various image analysis mechanisms to identify the food represented in the image data and one or more characteristics of the identified food (for example, nutritional information, ingredients, and the like). The server 110 also obtains medical information regarding the user, such as from an EMR 230 stored in the EMR system 115. Based on the medical information, the server 110 compares the characteristics of the food with the user's medical conditions to determine risks to the user in consuming the food. The server 110 may use medical knowledge repositories along with cognitive analysis to evaluate the risks, such as whether the food will cause symptoms to manifest, whether the ingestion of the food will exacerbate a medical condition, or the like. The analysis could be based on a metabolic model that is personalized for that patient based on parameters such as patient weight, age, stage of disease (such as Type 2 diabetes A1C) and other metabolic-related parameters. The analysis could also take into consideration physical activity based on wearable devices (such as a step counter). For example for a Type 2 diabetes patient, the system could provide the user with an option to perform 5,000 steps or take medication to regulate blood sugar levels to within safe levels.

The server 110 may transmit a notification specifying the risks (or the lack of risks) associated with ingesting the identified food to the user device 105, which outputs the notification to the user via the human-machine interface 150. The notification may be a visual message output via the display device 155, an audible message output via a speaker, a tactile message generated via a vibration engine, or a combination thereof. In some embodiments, the server 110 transmits the notification to the user device 105 originally submitting the image data. However, in other embodiments, the server 110 transmits the notification to a separate user device in addition to or as an alternative to transmitting the notification to the user device 105 submitting the image data.

For example, when a diabetic patient is about to eat a muffin, the server 110 may determine the ingredients of the muffin, nutritional information of the muffin, or a combination thereof (food characteristics) and compare the characteristics to information included in the patient's EMR 230, including known medical conditions of the patients. Accordingly, the server 110 may determine that muffin has a high sugar content, and, thus, the server 110 may issue a corresponding notification to the patient indicating that they should reconsider eating the muffin because of the high sugar content and the impact of such a sugar content on the patient's blood sugar level. In some embodiments, the server 110 may use current biological information regarding the patient, such as the patient's current blood sugar level, to determine risks and notifications. The biological information may be stored in the patient's EMR 230, provided from the user device 105, provided by the medical device 180, accessed from another data source, or the like. Also, in some embodiments, the server 110 uses individual patient metabolism information (included in the EMR 230 or provided by other systems or device) to determine consumption risks in a cognitive manner. Likewise, in some embodiments, the server 110 uses information about the individual user's activity level (e.g., physical activity) to evaluate consumption risk.

As another example, a person who is allergic to nuts may use the image capture device 140 to capture an image of a food, or food label, or recipe they intend to ingest. The user device 105 transmits the image data to the server 110, which analyzes the image data to identify the food represented in the image data and determine the ingredients in the food. The server 110 may determine that the food contains nuts as one of the ingredients. The server 110 will compare this characteristic with the user's EMR 230, which indicates that the user is allergic to nuts. Thus, the server 110 may issue a notification to the user indicating that the food contains nuts and there is a risk involved in consuming the food.

Figure 2:
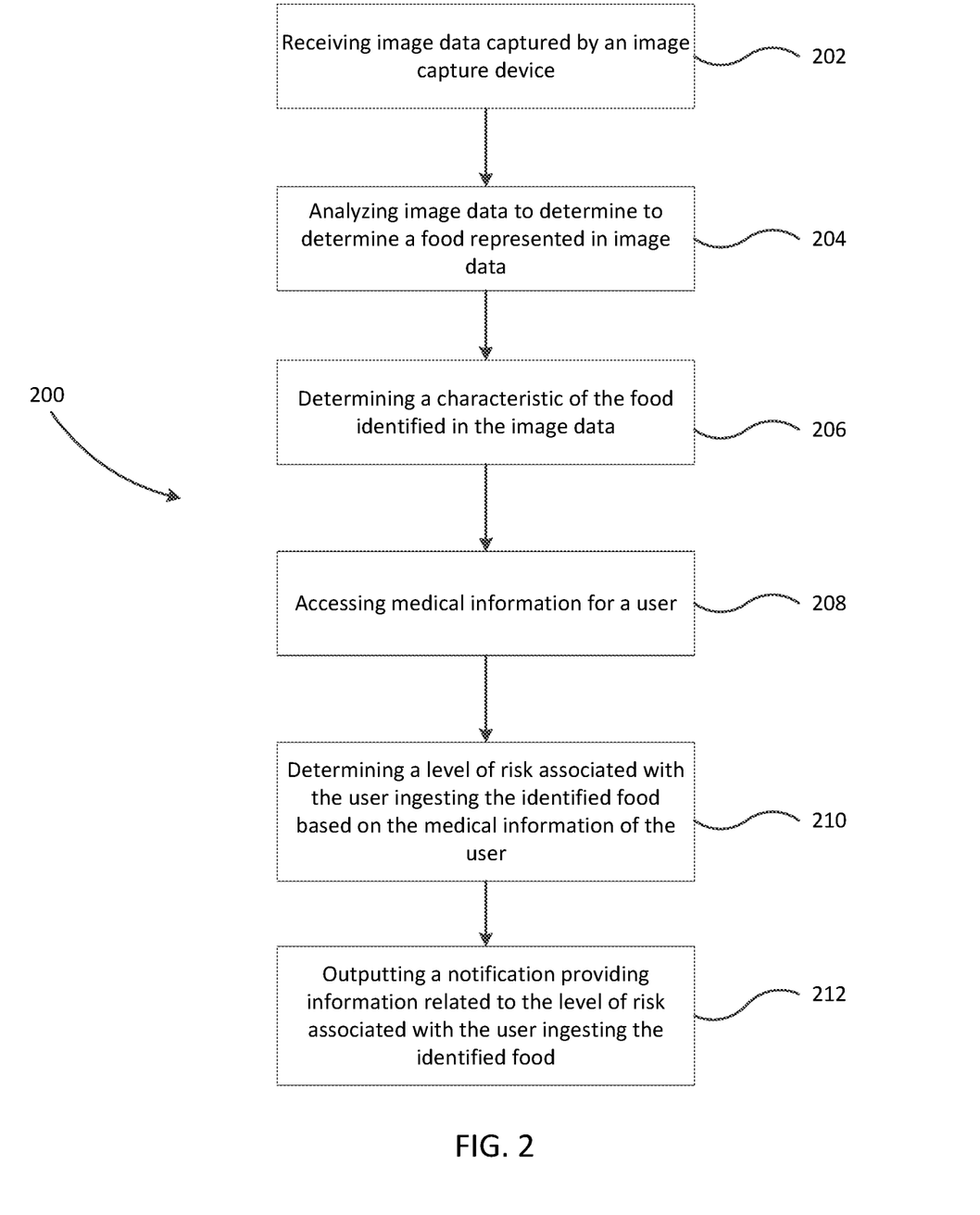
FIG. 2 is a flowchart illustrating a method of performing image-based analysis of food using the system of FIG. 1 and automatically alerting a user of a food that may conflict with a user's medical condition.

For example, FIG. 2 illustrates a method 200 of performing image-based analysis of food using the system 100 and automatically alerting a user of a food that may conflict with a user's medical condition according to one embodiment. The method 200 is described herein as being performed by the server 110 (the electronic processor 160 included in the server 110 executing software). However, as noted above, the method 200 or portions thereof may be locally performed by the user device 105 (the electronic processor 130 included in the user device 105 executing software).

As illustrated in FIG. 2, the method 200 includes receiving, with the electronic processor 160, image data captured via the image capture device 140 (at block 202). The electronic processor 160 analyzes the image data to automatically determine food represented in the image data (at block 204). The electronic processor 160 may use various image processing techniques to determine food represented in the image data, such as, for example, pattern recognition, digital geometry, machine/deep learning and signal processing. For example, the electronic processor 160 may be configured to perform image segmentation and recognize two-dimensional objects, three-dimensional objects, or both in segmented image data. The electronic processor 160 may then compare characteristics of recognized objects (such as, for example, size, shape, color, patterns, and the like) to characteristics of known objects to automatically determine food represented in the image data. Alternatively or in addition, the electronic processor 160 may be configured to compare the image data to image data of known foods to determine a match and, hence, a particular type of food represented in the received image data.

The electronic processor 160 may access various knowledge bases (databases, libraries, services, or the like) to identify food in image data. The knowledge bases used to automatically identify food in image data may be built using machine learning and artificial intelligence technologies. For example, in some embodiments, users may submit image data representing food with metadata describing the food and, optionally, other objects in the image. Accordingly, the electronic processor 160 (or a separate server or system) may use this received data as training data to perform machine learning. Machine learning generally refers to the ability of a computer program to learn without being explicitly programmed. In some embodiments, a computer program is configured to construct a model (one or more algorithms) based on example inputs. Supervised learning involves presenting a computer program with example inputs and their desired (for example, actual) outputs. The computer program is configured to learn a general rule (a model) that maps the inputs to the outputs. The computer program may be configured to perform machine learning using various types of methods and mechanisms. For example, the computer program may perform machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics. Accordingly, the server 110 may be configured to use image analysis techniques established using machine learning and may further refine the techniques based on feedback received from a user or other sources.

After determining the food represented in the image data, the electronic processor 160 determines characteristics for the food represented in the image data (at block 206). The characteristics for the food may include ingredients, nutritional data, and the like. The server 110 may access one or more knowledge bases (included in the server 110 or external the server 110) to determine the characteristics. For example, the electronic processor 160 may access a food database (included in the server 110 or external to the server 110) containing a library of foods that associates a plurality of different foods with an associated food characteristic, such as nutritional information, ingredients, and the like. In some embodiments, the server 110 also uses the image data to determine the characteristics, such as by determining a size of a particular food item, which may impact the nutritional data (which may be specified on a per serving basis).

The electronic processor 160 also accesses medical information of a user (at block 208). The server 110 may access the user's EMR 230 as stored in the EMR system 115 to access the medical information. Alternatively or in addition, the server 110 may locally store the medical information or may receive the medical information from the user device 105.

The electronic processor 160 also determines a level of risk associated with the user ingesting the food identified in the image data based on the medical information of the user (at block 210) and outputs a notification providing information related to the level of risk associated with the user ingesting the food identified in the image data (at block 212). For example, the electronic processor 160 may compare the characteristics of the food with the medical information for the user to determine the level of risk. Comparing the food characteristics with the medical information may include looking for ingredients in the food that the user is allergic to, determining whether a nutritional aspect of the food (sodium amount, calorie amount, sugar amount, and the like) is within an acceptable range for the user's diet, and the like. The electronic processor 160 may also consider additional information in determining the level of risk. For example, the electronic processor 160 may consider biological information of the user (heart rate, blood sugar level, or the like), a time of day, a time of last medication, or the like. Additionally, the electronic processor 160 may evaluate the level of risk based on health targets, such as a weight target, to determine whether the food identified in the image data is consistent with the health target of the user. Accordingly, in some embodiments, the level of risk is personized, meaning that the same food identified in image data will result in a different level of risk for different users, depending on each user's medical information, a user's current biological information, metabolism information for the user, or a combination thereof.

As described above, the notification may be a visual message output via the display device 155, an audible message output via a speaker on the user device 105, a tactile message generated via a vibration engine, or a combination thereof. As also noted above, in some embodiments, the electronic processor 160 outputs the notification by transmitting the notification to the user device 105 originally submitting the image data. However, in other embodiments, the electronic processor 160 alternatively or in addition outputs the notification by transmitting the notification to a different user device 105 than the user device 105 submitting the image data separate user device 105. For example, the user device 105 submitting the image data may be a smart wearable or smart scale, and the electronic processor 160 may be configured to output the notification to a smart phone (to take advantage of a larger display device provided by the smart phone). Similarly, the electronic processor 160 may be configured to output a notification to a caregiver (a parent, a physician, or the like) based on image data captured by a patient. Similarly, the electronic processor 160 may access medical information for a user associated with the user device 105 submitting the image data (and receiving the notification) or a separate user. For example, a parent may use the image capture device 140 to capture an image and submit the original image data to the server 110 on behalf of a child. Accordingly, in this situation, the electronic processor 160 determines a level of risk as described above for the child (as compared to for the parent).

The notification may include an indication of the level of risk the food poses for the user. For example, the notification may inform the user whether there is a high, medium, or low risk associated with the food. Additionally, the notification may inform the user of the type of risk associated with the food, for example, whether the food is high fat, high calorie, high sugar, high sodium, or the like. Alternatively, the notification may indicate a positive level of risk associated with the food, such as being, an anti-inflammatory food, high protein, high fiber, high vitamins, or the like. The positive level of risk associated with the food can vary depending on the EMR of the particular user. For example, a certain medical condition may have a positive correlation with certain characteristics of food, such as a need for high fiber foods. Similarly, the notification may include a warning that the food contains an ingredient that the user is allergic to or intolerant of. In this case, the notification may include a warning not to consume the food at all due to a high risk of a negative reaction to the food.

In some embodiments, the notification also includes a recommendation for addressing the determined level of risk. For example, the electronic processor 160 may determine an amount of physical exercise that can be done by the user to mitigate the level of risk associated with the food and this information may be included in the notification. Alternatively or in addition, the notification may include a type and dosage of medicine that should be taken to off-set the risk associated with the food. For example, a notification may notify the user that if the user consumes the identified food that the user should inject a certain dose of insulin. Similarly, the notification may notify the user that the food includes a certain ingredient that the user is intolerant of (for example, milk), and inform the user that the user should take a medication (for example, lactose intolerance medication) prior to, with, or after consuming the food.

Figure 3:
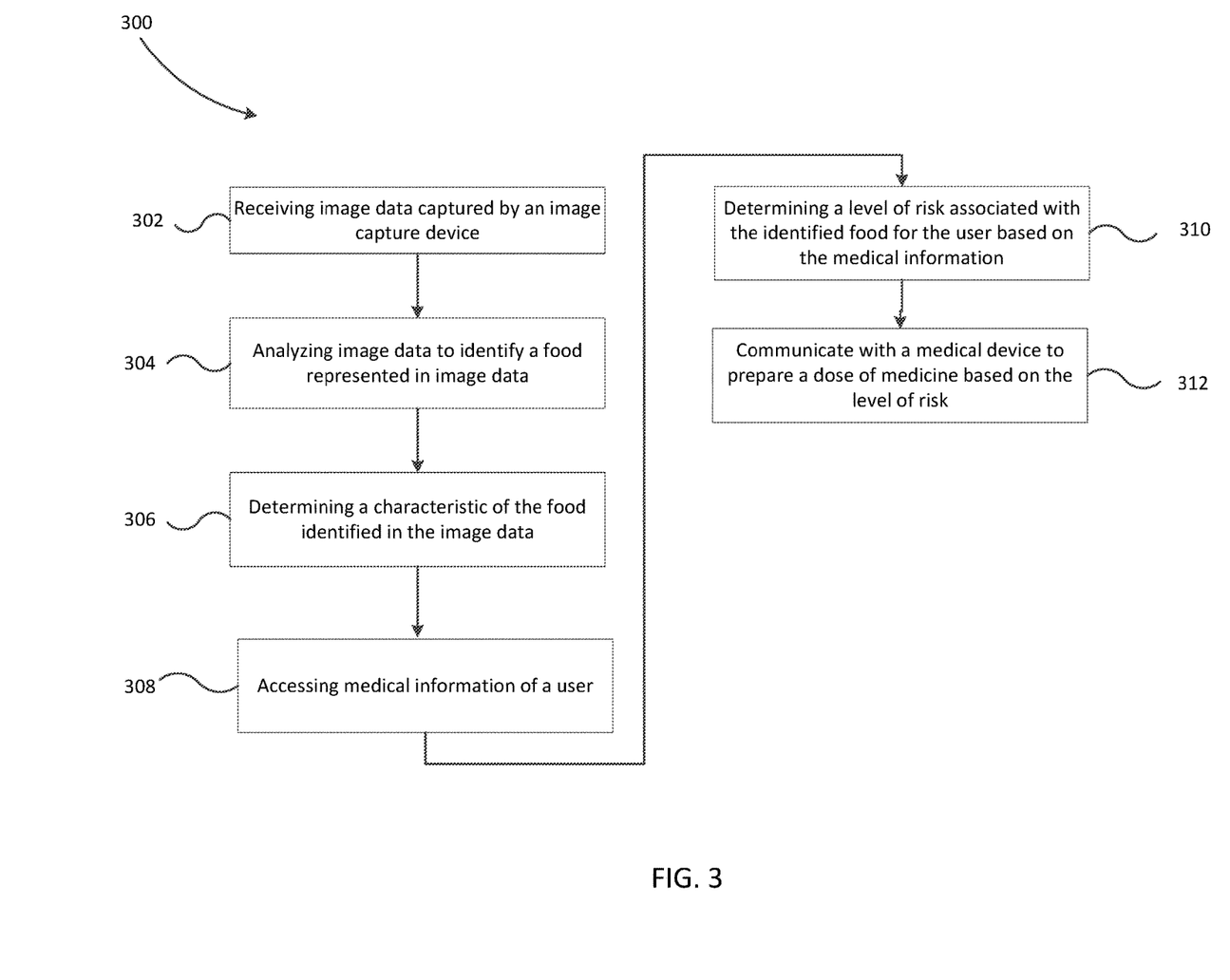
FIG. 3 is a flowchart illustrating another method of performing image-based analysis of food using the system of FIG. 1.

As previously mentioned, in some embodiments, the system 100 includes a medical device 180 to assist the user in administering medication. FIG. 3 illustrates a method 300 of performing image-based analysis of food using the system 100 wherein the system 100 includes the medical device 180. Portions of the method 300 are similar to portions of the method 200 and, thus, should be understood to have similar attributes. Again, the method 300 is described as being performed by the server 110 (the electronic processor 160 executing software), but, in other embodiments, all or a portion of this functionality may be performed by other devices, such as the user device 105, the medical device 180, or a combination thereof.

As illustrated in FIG. 3, the method 300 includes receiving, with the electronic processor 160, image data captured via the image capture device 140 (at block 302). As described above with response to FIG. 2, the electronic processor 160 analyzes the image data to identify food represented in the image data (at block 304), determines characteristics of the identified food, such as by accessing a food database (at block 306), accessing medical information for a user (at block 308), and determining a level of risk for the user if the user were to ingest the identified food based on the user's medical information (at block 310).

As illustrated in FIG. 3, in addition to or as an alternative to outputting a notification as described above, the electronic processor 160 communicates with the medical device to prepare a dosage of medicine based on the level of risk (at block 312). For example, the electronic processor 160 may communicate with the medical device 180 to receive confirmation of whether the user consumed the identified food. In particular, the electronic processor 160 may use biological information detected by one or more sensors included in the medical device 180 to confirm whether the user consumed the identified food. Alternatively or in addition, the electronic processor 160 may prompt a user (via a user device 105) to confirm whether the identified food was consumed. Accordingly, after receiving confirmation that the user consumed the identified food, the electronic processor 160 can communicate with the medical device 180 to instruct the medical device 180 to administer the appropriate medication and dose.

For example, the electronic processor 160 may instruct the medical device 180 to prepare a certain dose of medication for the user to inject. The medical device 180 may use the medicine administrator 220 to prepare the dose of medication. For example, the medical device 180 may prepare a dose of insulin in a needle for a diabetic user to administer before or after consuming the food identified in the image data. In some embodiments, the medicine administrator 220 prepares and automatically administers the medication to the user. For example, the medicine administrator 220 may be implanted in the user and may receive instructions from the one of both of the electronic processor 160 or the medical device 180 to inject a dose of medicine into the user.

Also, in some embodiments, the electronic processor 160 communicates with the medical device 180 to indicate that a food consumed by the user has a specified level of risk and instructs the medical device 180 to monitor a characteristic of the user. For example, the electronic processor 160 may instruct the medical device 180 to monitor the blood glucose level of a diabetic user after the user consumes a donut. When the user's blood glucose level reaches a predetermined level, the medicine administrator 220 can inject insulin into the user's blood to mitigate the risk associated with the consumption of the donut. In such an embodiment, the system 100 may also use machine learning to create a personalized metabolism model for a particular user that can be used to provide a personalized level of risk. For example, as the medical device 180 monitors the user's glucose level, the electronic processor 160 may learn how a particular user reacts to certain foods. Accordingly, such monitoring allows the electronic processor to apply a further level of personalization to the determination of a level of risk for a particular user as described above.

Again, it should be understood that the functionality described herein with respect to the server 110 (or a portion thereof) may be performed locally by the user device 105. For example, the user device 105 may store (in the memory 135) image-analysis software that automatically identifies and determines characteristics of food represented in image data. The user device 105 may then compare the determined food characteristics to a user's medical information, which may be stored in the EMR system 115 as described above, stored locally on the user device 105, or stored on a separate device communicatively coupled with the user device 105. Accordingly, in some embodiments, the user device 105 may store and execute a dedicated software application for analyzing images and providing alerts as described herein with or without communicating with one or more external devices or systems.

Thus, embodiments described herein provide systems and methods for automatically correlating food and food characteristics identified in image data with a user's medical information, such as medical conditions, to automatically determine a level of risk associated with ingesting the food and automatically alert the user of the determined level of risk. Thus, a user is able to make better decisions regarding his or her diet using up-to-date information and cognitive systems.

Various features and advantages of the invention are set forth in the following claims.

What is claimed is:

1. A method of performing image based analysis of food, the method comprising:
   receiving, with an electronic processor, image data captured by a first image capture device operated by a first user;
   analyzing the image data, with the electronic processor, to identify a food represented in the image data;
   determining, with the electronic processor, a characteristic of the food identified in the image data;
   accessing, with the electronic processor, medical information of a second user;
   determining, with the electronic processor, a level of risk associated with the second user ingesting the food identified in the image data based on the medical information of the second user, and
   outputting, with the electronic processor, a notification, the notification providing information related to the level of risk associated with the second user ingesting the food identified in the image data.

2. The method of claim 1, wherein determining the characteristic of the food identified in the image data includes identifying at least one of nutritional information of the food and an ingredient of the food.

3. The method of claim 1, wherein outputting the notification includes transmitting the notification to a user device, wherein the notification includes at least one selected from a group consisting of visual message output via a display device of the user device, an audible message output via a speaker of the user device, and a tactile message generated via a vibration engine of the user device.

4. The method of claim 1, wherein outputting the notification includes outputting the notification via a user device, wherein the electronic processor is included in the user device.

5. The method of claim 1, wherein outputting the notification includes outputting a notification including a recommendation for mitigating the level of risk.

6. The method of claim 5, wherein outputting the notification including the recommendation for mitigating the level of risk includes outputting a notification including at least one of a recommendation of a type of medication the second user should take and a dosage of the medication the second user should take.

7. The method of claim 1, further comprising communicating with a medical device delivering medication to the second user, wherein communicating with the medical device includes communicating with the medical device through a user device.

8. The method of claim 7, wherein communicating with the medical device includes receiving confirmation from the medical device that the second user ingested the food identified in the image data and transmitting instructions to the medical device to prepare a dose of the medication to the second user.

9. The method of claim 7, wherein communicating with the medical device includes receiving confirmation from the medical device that the second user ingested the food identified in the image data and transmitting instructions to the medical device to prepare and automatically administer a dose of the medication to the second user.

10. The method of claim 1, wherein accessing medical information of the second user includes accessing an electronic medical record of the second user.

11. Non-transitory computer readable medium storing instructions that, when executed by an electronic processor, perform a set of functions, the set of functions comprising:
    receiving image data captured by a first image capture device;
    analyzing the image data to identify a food represented in the image data;
    determining a characteristic of the food identified in the image data by accessing a food database containing a library of foods and associated characteristics of the foods;
    accessing medical information of a first user;
    determining a level of risk associated with the first user ingesting the food identified in the image data based on the medical information of the first user;

communicating with a medical device to prepare a dosage of medicine based on the level of risk, and outputting a notification to a second user device operated by the second user related to the level of risk associated with the first user ingesting the food.

\* \* \* \* \*